US005370113A

United States Patent [19]

Parsons

[11] Patent Number: 5,370,113

[45] Date of Patent: Dec. 6, 1994

[54] BREATHING APPARATUS HELD IN A CONVERTIBLE CASE AND GARMENT ASSEMBLY

[75] Inventor: Patrick Parsons, Purley, England

[73] Assignee: Racal Panorama Limited, Berkshire

[21] Appl. No.: 850,618

[22] Filed: Mar. 13, 1992

[30] Foreign Application Priority Data

Mar. 20, 1991 [GB] United Kingdom .............. 9105925.3
Apr. 10, 1991 [GB] United Kingdom .............. 9107523.4

[51] Int. Cl.[5] ........................ A61M 15/00; A62B 7/00; A41D 1/04; B63C 11/02

[52] U.S. Cl. ........................... 128/205.22; 128/202.13; 128/202.19; 2/102; 2/DIG. 2; 405/186; 441/125; 441/106; 224/151; 224/153

[58] Field of Search ....................... 128/204.18, 201.27, 128/201.28, 201.29, 202.13, 202.19, 204.26, 205.22; 224/151, 153; 2/1, 102, DIG. 2; 405/185, 186; 441/106, 125, 136

[56] References Cited

U.S. PATENT DOCUMENTS

| | | | |
|---|---|---|---|
| 911,389 | 2/1909 | Garforth . | |
| 996,135 | 6/1911 | Poe . | |
| 1,009,083 | 11/1911 | McNamee . | |
| 2,409,354 | 10/1946 | Grunwell . | |
| 2,456,130 | 12/1948 | Lambertsen . | |
| 3,135,098 | 6/1964 | Root . | |
| 3,266,489 | 5/1963 | Williams . | |
| 4,090,509 | 5/1978 | Smith . | |
| 4,324,234 | 4/1982 | Maness | 128/202.14 |
| 4,475,251 | 10/1984 | Hopkins | 2/94 |
| 4,685,456 | 8/1987 | Smart | 128/204.18 |
| 4,739,913 | 4/1988 | Moore | 224/215 |
| 4,752,263 | 6/1988 | Pritchard et al. | 441/88 |
| 4,986,700 | 1/1991 | Takeda | 405/186 |

FOREIGN PATENT DOCUMENTS

| | | |
|---|---|---|
| 0111634 | 6/1984 | European Pat. Off. . |
| 0269578 | 6/1988 | European Pat. Off. . |
| 1210327 | 2/1966 | Germany . |
| 432249 | 9/1967 | Switzerland . |
| 2056260 | 3/1981 | United Kingdom . |
| 2231254A | 11/1990 | United Kingdom . |
| WO84/01092 | 3/1984 | WIPO . |

*Primary Examiner*—Kimberly L. Asher
*Attorney, Agent, or Firm*—Anna E. Mack

[57] ABSTRACT

A self contained breathing apparatus comprises a compressed air cylinder, facemask and hose which when not in use are stored and carried within a case formed from an assembly of flexible sheet material. The elements of the case are constructed such that when it is opened and reversed it is adapted to form a garment to be worn over the torso and support the air cylinder for use.

8 Claims, 4 Drawing Sheets

BREATHING APPARATUS HELD IN A CONVERTIBLE CASE AND GARMENT ASSEMBLY

BACKGROUND

The present invention relates to self-contained breathing apparatus such as may be worn to sustain the respiration of its user in noxious or oxygen-depleted environments. Such apparatus conventionally includes a portable source of breathing gas (e.g. a compressed air cylinder) and breathing interface means (e.g. a full or partial facemask) through which the breathing gas is in use supplied from said source to the respiratory passages of the user at a regulated rate.

In the case of self-contained open-circuit compressed air breathing apparatus it is usual for the air cylinder(s) to be carried on the back of the user, being mounted for this purpose on a plate or frame attached to a body harness comprised of strong webbing which passes over the user's shoulders and around his waist. As an alternative to this form of harness, it is known to support the cylinder on the back of a jerkin-type garment. Breathing sets are also known where an air cylinder is slung by a strap across one shoulder to be worn at the hip, but this arrangement is only suitable for relatively small and light cylinders, consequently providing very short endurance. A back-carrying harness arrangement is generally preferred because the weight of the cylinder(s) is distributed symmetrically and at a position which impedes the movements of the user the least.

SUMMARY OF THE INVENTION

In one aspect, the present invention seeks to provide a self-contained breathing apparatus with means for its storage and transportation when not in use and which, by suitable conversion when the apparatus is to be donned for use, avoids the need for a separate supportive harness. The invention has been developed in particular for use with open-circuit compressed air breathing apparatus of the kind generally known as "inspection" or "escape" sets using a cylinder of typically 3 to 6 liters capacity which will provide a nominal endurance of, say, 15 to 30 minutes. However, the invention is by no means limited to such usage and in principle may be used in conjunction with any size or form of portable breathing gas source which is capable of being supported on the torso. In particular, in addition to open-circuit compressed air (or oxygen) breathing apparatus the invention may find application to the closed-circuit regenerative type of self-contained oxygen breathing apparatus.

Accordingly in one aspect the invention resides in self-contained breathing apparatus comprising a portable source of breathing gas and breathing interface means through which the breathing gas is in use supplied from said source to the respiratory passages of the user at a regulated rate, together with an assembly of flexible sheet material which can be folded and closed to form a case enclosing at least said gas source when not in use and which when opened and reversed is adapted to form a garment to be worn over the torso and to support the gas source for use, preferably on the back of the user.

In a preferred embodiment the case encloses a complete breathing circuit ready for use subject to opening the case, donning the garment and breathing interface means, and opening a valve to release breathing gas from the source thereof to the interface means. The garment which the flexible sheet material is adapted to form preferably is in the nature of a jerkin (vest) which is donned by passing the arms through respective holes and closing together two sides across the chest.

A preferred embodiment of the invention will now be more particularly described, by way of example, with reference to the accompanying drawings.

DETAILED DESCRIPTION OF THE PREFERRED EMBODIMENT

The following particular description indicates the sequence of operations which is performed to convert the illustrated breathing apparatus, which is of the open-circuit compressed air kind, from its stored mode into its operational mode.

Figure 1:
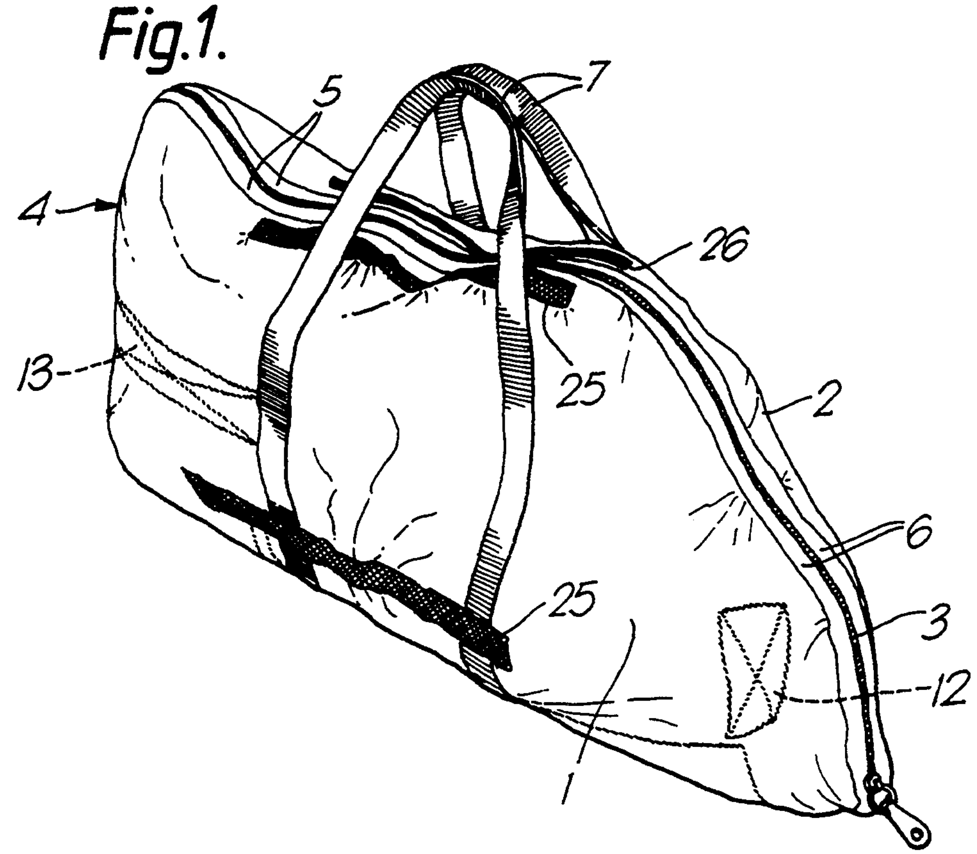
FIG. 1 is a perspective view of the case within which the remainder of the apparatus can be carried.
Figure 2:
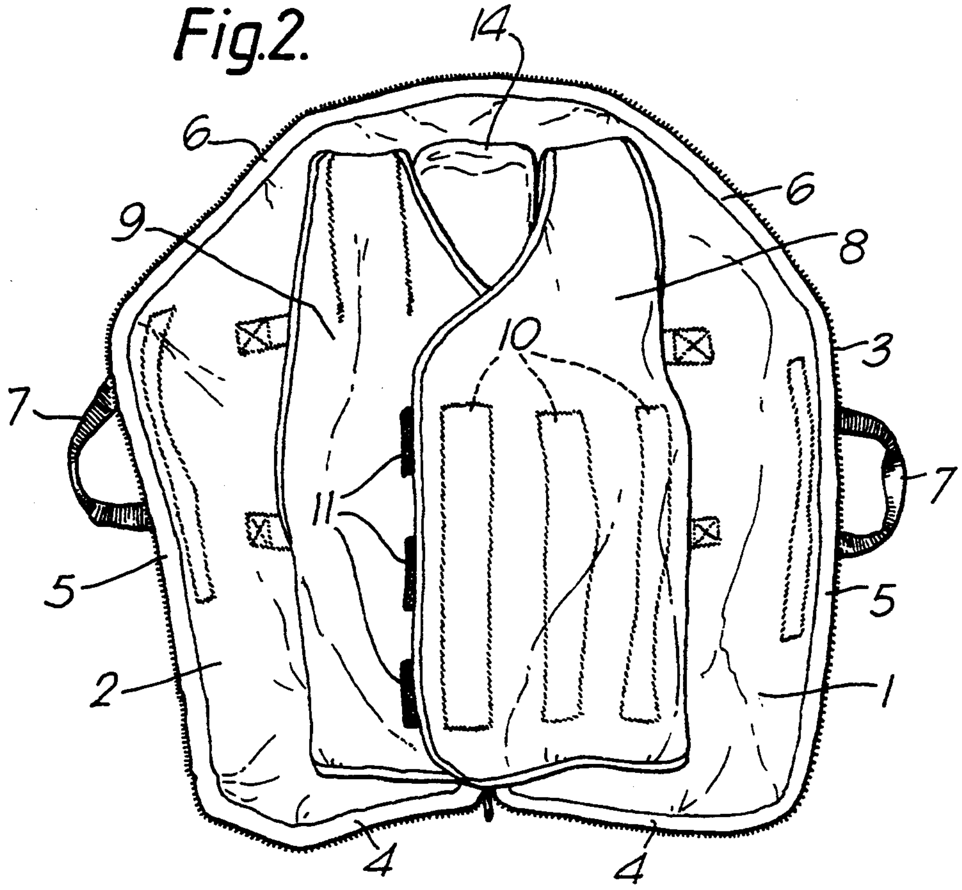
FIG. 2 is a plan view of the apparatus with the case opened and its side flaps unfolded.

Referring to FIG. 1, the illustrated case is formed from a single piece of synthetic fabric, such as the multilayer, flame resistant, plasticised PVC on polyester fabric known as CAFLEX FP600FR, (CAFLEX is a trade mark of Coating Applications (Textiles) Limited). In principle, however, any natural or synthetic fabric that will support the weight of the breathing apparatus and meet other relevant performance criteria may be used. This case has two folded-up side flaps 1 and 2 which are held together along the length of their upper (as viewed) edges by a zip fastener 3. More particularly, and as also indicated in FIG. 2 which shows the flaps 1 and 2 unfolded, the flap edges which are united in the FIG. 1 condition have respective generally straight lengths 4 at the rear (as viewed) of the case leading to second generally orthogonal straight lengths 5 at the top of the case and inclined lengths 6 at the front (as viewed) of the case. Loops of webbing 7 are sewn on to provide handles for hand-carrying the case. Alternatively, longer loops may be provided if it is preferred to carry the case over the shoulder.

FIG. 2 shows the apparatus after releasing the zip fastener 3 and unfolding the side flaps 1 and 2, their inner surfaces now being seen. It is assumed that the apparatus is laid out on a floor, table or other flat surface. Revealed inside the case are two inner flaps 8 and 9, folded one over the other and held together by respective perpendicular strips 10,11 of the synthetic fibre fastening material known as VELCRO, (VELCRO is a registered trade mark of Selectus Limited). The inner flaps 8 and 9 are made from respective pieces of the same material as forms the outer flaps 1 and 2 and are respectively attached to the outer piece at their top and lower-side edges, at the regions indicated by the stitched patches 12 and 13 in FIGS. 3 and 4. The regions between the patches 12 and 13 where the flaps 8 and 9 are not attached to the outer piece will form the arm holes 27 and 28 of FIG. 5 when the garment is ready for donning. Also seen in FIG. 2 is the top of the cylinder pouch 14 which is revealed in its entirety in FIG. 3.

Figure 3:
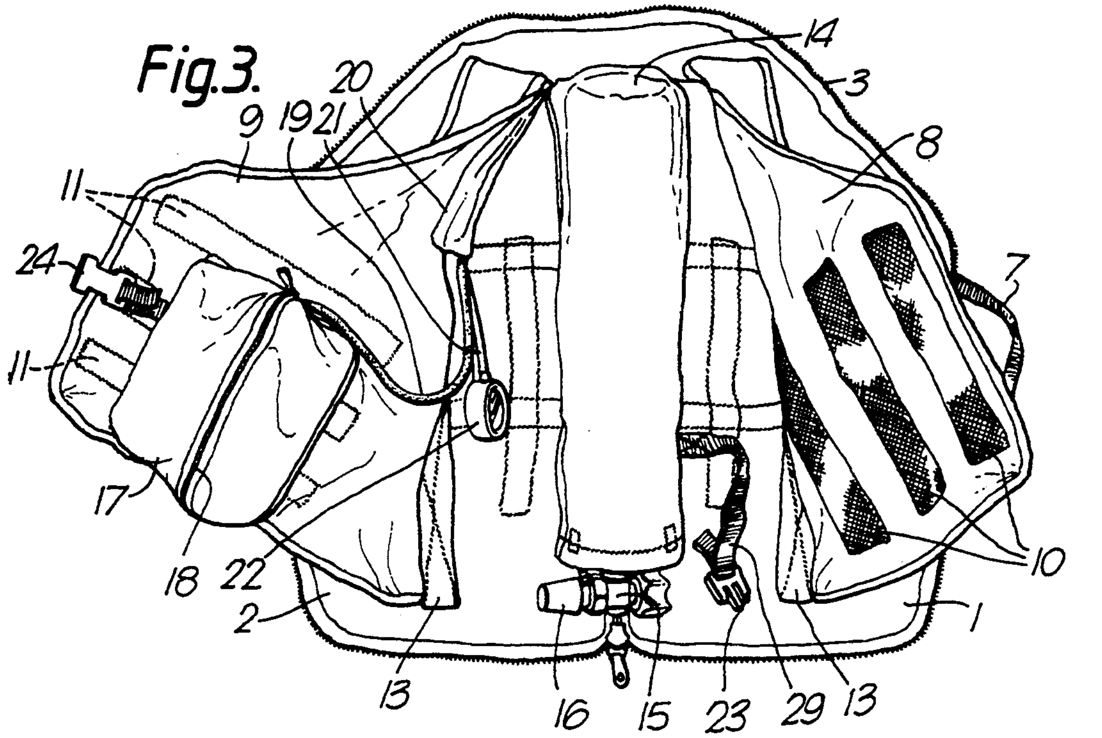
FIG. 3 is a plan view of the apparatus following from the condition of FIG. 2, with two inner flaps unfolded.

FIG. 3 shows the apparatus after separating and folding back the inner flaps 8 and 9. A pouch 14 is sewn centrally to the outer piece of fabric, at a position which lies along the base of the case in FIG. 1. This pouch is open at its lower (as viewed) end to receive a compressed air cylinder which is hidden from view in FIG. 3 apart from its on/off valve fitting 15 and attached first-stage pressure reducer 16. Another pouch 17, closed by a central zip fastener 18, is sewn onto the now-revealed side of the inner flap 9, which houses a facemask fitted with a demand valve; (these items will be seen at 30 and 31 in FIG. 7). A low-pressure hose 19 leads up through the cylinder pouch 14 from the low-pressure side of the pressure reducer 16 and down through a fabric guide 20 to the facemask demand valve in pouch 17. A high-pressure hose 21 leads in parallel to the hose 19, but from the high-pressure side of the fitting 16, to a conventional cylinder contents (pressure) gauge and low-pressure warning whistle assembly 22. Also seen in FIG. 3 are the two parts of a waist clip fastener 23,24 which will be attached together when the apparatus is donned.

Figure 4:
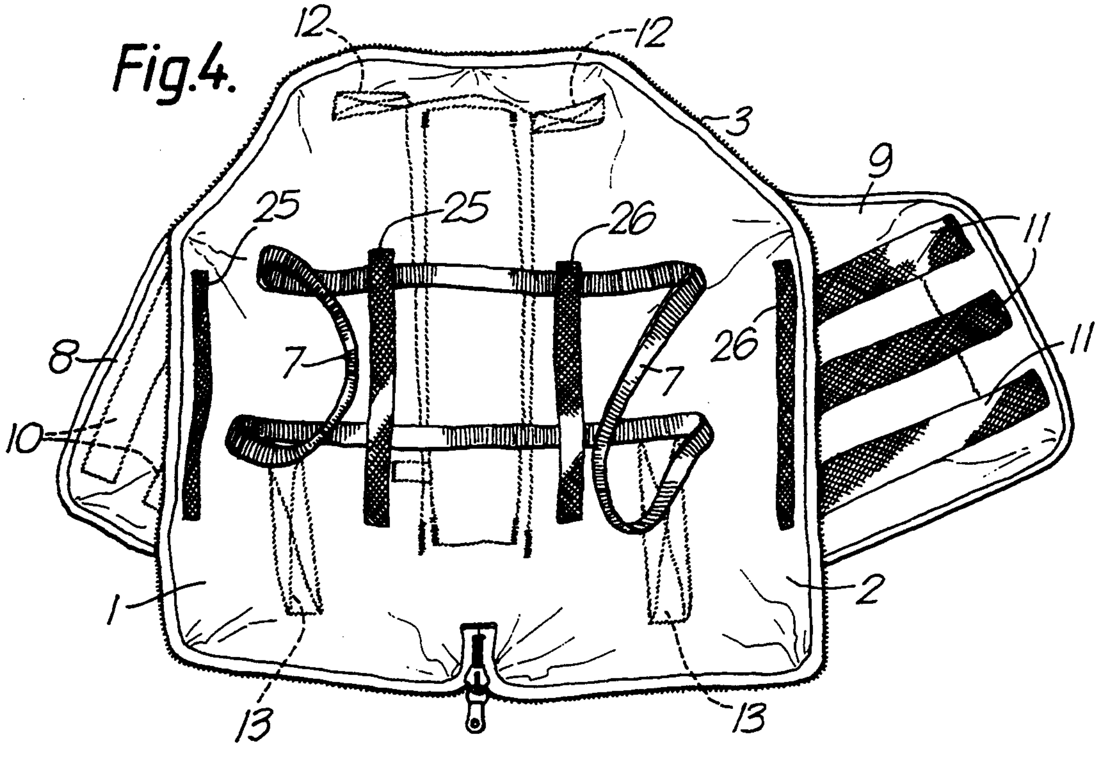
FIG. 4 is a plan view of the apparatus turned over from the condition of FIG. 3.
Figure 5:
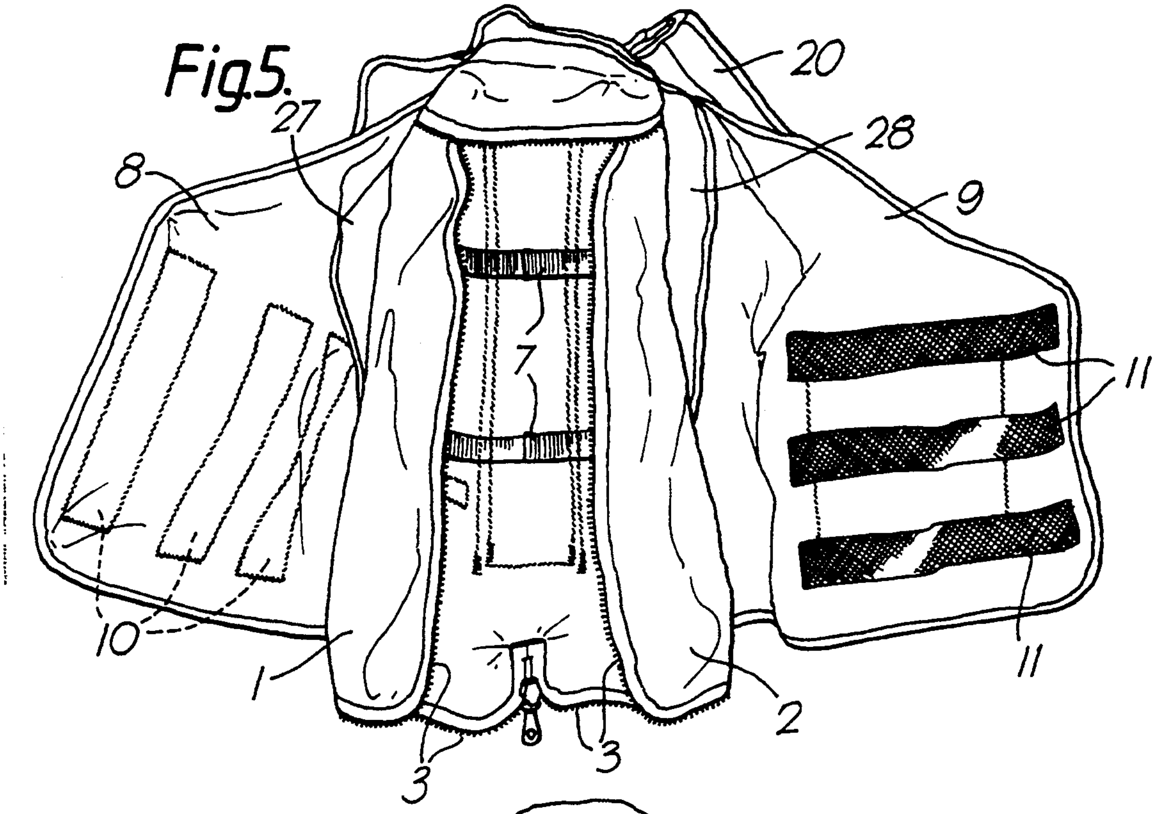
FIG. 5 is a plan view of the apparatus following from the condition of FIG. 4, with the originally outer flaps folded inwards, and the garment now ready for donning.

FIG. 4 shows the apparatus after turning it over bodily from its FIG. 3 condition. From this condition the two side flaps 1 and 2 of the case are folded in on themselves as shown in FIG. 5, with the respective carrying handles 7 trapped between. These flaps are held in the folded-in condition by respective pairs of VELCRO strips 25,26 seen in FIG. 4. With the flaps 1 and 2 folded in and their top edges tucked out through the arm holes 27,28 as shown in FIG. 5, the apparatus is ready for donning. The three fabric pieces ½, 8 and 9 collectively define a jerkin or vest, of which the back is provided by the folded piece ½, (which originally defined the case of FIG. 1), and the two sides are provided by respective "inner" flaps 8 and 9 (which are now, of course, on the outside). As previously indicated, the arm holes 27,28 seen in FIG. 5 are defined between the patches 12 and 13 where the respective flaps 8 and 9 are stitched to the flaps 1 and 2.

Figure 6:
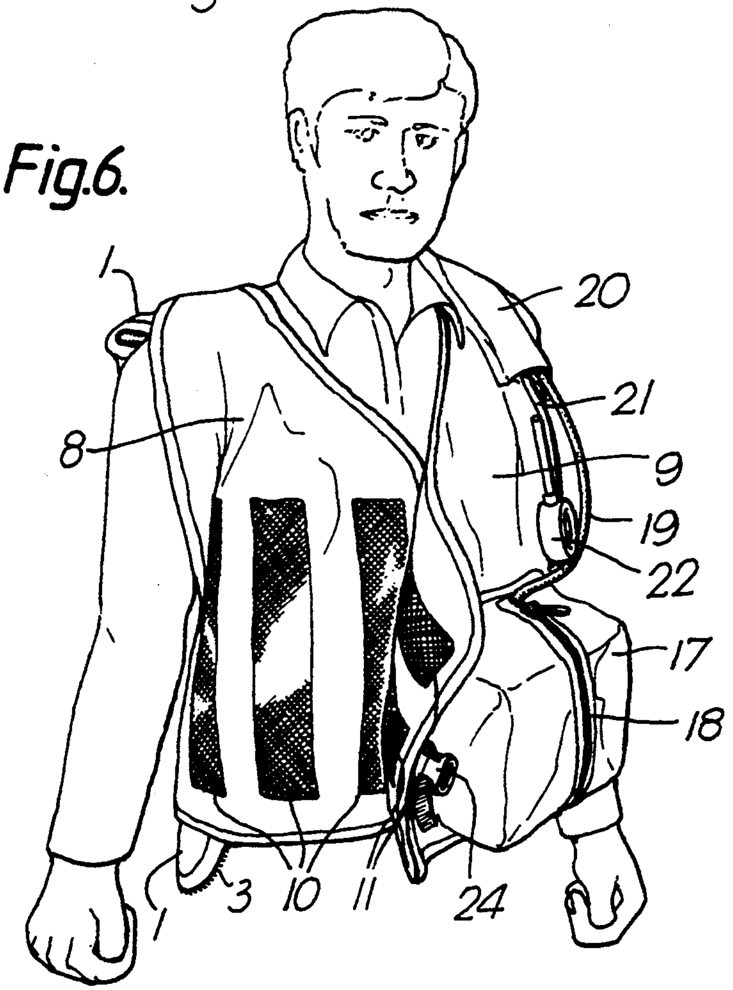
FIG. 6 is a perspective view showing the garment during donning.
Figure 7:
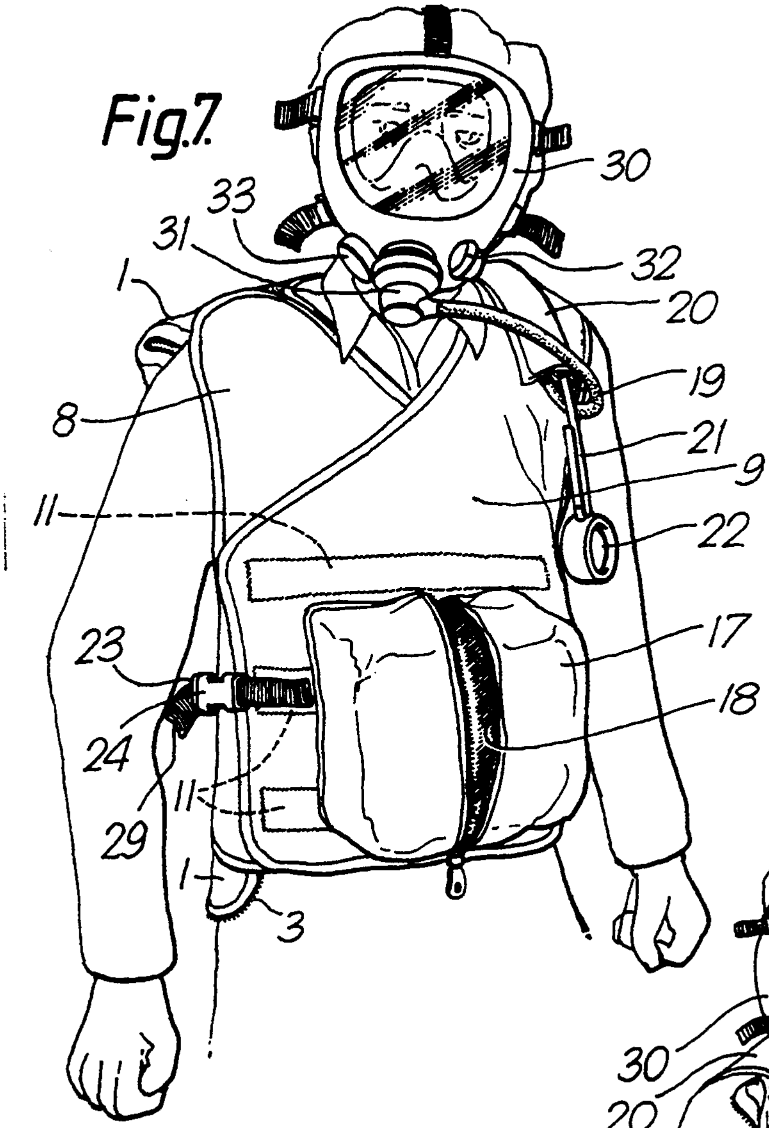
FIGS. 7 and 8 are respective perspective views from the front and rear showing the breathing apparatus in use.

The jerkin is donned by the user passing his right and left arms respectively through the arm holes 27 and 28 so that the folded-in flaps 1,2 lie along his back on the inside of the garment, with the cylinder pouch 14 of course now being located on the outside. Flap 8 is folded across his chest from the right (as worn) and flap 9 is folded across the top of the flap 8 from the left. For ease of illustration FIG. 6 shows the jerkin donned and flap 9 partially folded over. The flaps 8 and 9 are held together across the chest by interengaging VELCRO strips 10 and 11, their perpendicular orientation permitting engagement over a wide range of different chest sizes. The fastening is completed by clipping together the two parts of the fastener 23,24 as shown in FIG. 7 adjusting if required by pulling through the length of webbing 29 by which the fastener part 23 is attached to the flap 1 (see also FIG. 3). The principal fastening of the flaps 8 and 9 around the body of the user is achieved by the VELCRO strips 10 and 11, however, the fastener 23,24 serving only as a safety device to prevent the accidental tearing open of the VELCRO connection.

With the jerkin thus donned, the facemask pouch 17 is now located on the chest of the user. The zip fastener 18 is released to permit removal and donning of the facemask 30 as shown in FIG. 7. It is shown in this Figure fitted with a positive-pressure demand valve 31 connected to the hose 19, an exhalation valve 32 and speech transmission diaphragm 33. The breathing circuit remains connected up while the apparatus is in its storage mode so all that is required to put it into operation is for the user to don the facemask and turn on the air supply from the cylinder by turning the handwheel of the valve 15 seen in FIG. 8. The air cylinder may be supported within the pouch 14 by any convenient means, such as by a ring around the neck of the (inverted) cylinder attached by dog clips to rings sewn into the open (lower) end of the pouch.

After use and any replacement or recharging of the air cylinder, the apparatus is returned to its storage mode within the bag of FIG. 1 by reversal of the procedure described above.

Figure 8:
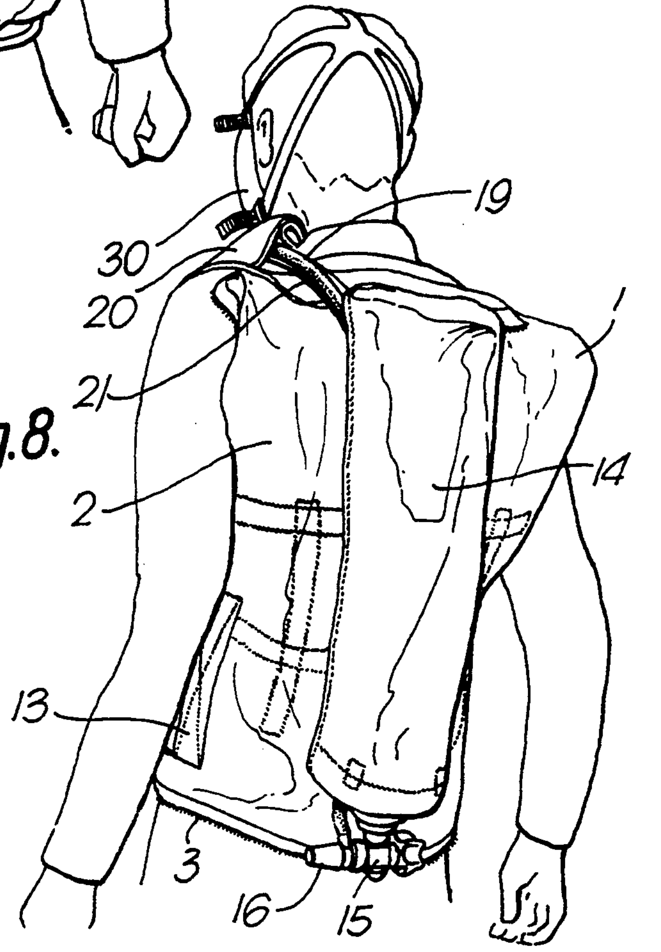

The guide 20 seen most clearly in FIG. 6–8 is formed from a loop of fabric and made large enough for the pressure reducer 16 and hoses 19,21 (or gauge/whistle 22 and hoses) to pass through it. The loop is then folded on itself and held together by VELCRO strips so that when in use the hoses are held firmly in position.

A particular advantage of the illustrated apparatus is that the whole breathing circuit is held in place by the design of the garment and no tools are required to remove it from the garment when cleaning or disinfection/decontamination is to be carried out.

I claim:

1. A self-contained breathing assembly comprising:

a portable source of breathing gas;

breathing interface means adapted to be worn by a user for supplying breathing gas to the respiratory passages of the user;

conduit means connected to said source and to said interface means defining a flowpath for leading breathing gas from said group to said interface means;

means for opening and closing said flowpath; and a reversibly convertible assembly being in a first configuration a case, and in a second configuration a garment, said reversibly convertible assembly in said case configuration having a size and strength to enclose said gas source, interface means, conduit means, and means for opening and closing said flowpath, for storage and transportation of said breathing assembly with said conduit means connected as aforesaid and said flowpath closed, said reversibly convertible assembly in said garment configuration adapted to be worn over the torso of a user, and supporting said gas source when in use;

said reversibly convertible case and garment assembly further comprising:

a first element of flexible sheet material having at least two mating edges foldable to place said edges in close proximity to form said case;

first fastening means for maintaining said edges in close proximity when said case is closed;

second and third elements of flexible sheet material each of which is attached to said first element in the region of a respective one of said mating edges thereof;

second fastening means for association with said second and third elements; and supporting means for said gas source attached to said first element;

said second and third elements being positioned to lie interiorly of said case when said case is closed but, when said case is opened, and reversibly converted to said garment configuration said second and third elements defining flaps to fold forwardly around the user's torso while said first element lies at the rear of the user's torso with a surface of said first element which defines an interior surface of said case defining an exterior surface of said garment and arm holes being formed between said first element and said second and third elements respectively;

said second fastening means being operable to hold said flaps in place when folded forwardly around the user's torso;

and said supporting means being configured to position said gas source along a base region of said case and to support said gas source in a vertical position upon the user's back when said assembly is reversibly converted into said garment;

whereby said breathing apparatus is ready for use by the user subject to opening said case, converting said case into said garment, donning said garment and interface means, and placing said means for opening and closing said flowpath in an open position.

2. The breathing assembly of claim 1 further comprising a means for guiding said conduit means between said source of breathing gas and said interface means located interiorly of said first element when said case is closed and exteriorly of said first element when said case is opened.

3. A breathing assembly comprising a complete self-contained breathing apparatus ready for use, subject to releasing breathing gas from a portable source of breathing gas provided therein, of the type comprising: a portable source of breathing gas, breathing interface means for supplying the breathing gas in use from said source of breathing gas to the respiratory passages of the user, conduit means connected between said source and said interface means to define a flowpath for leading said breathing gas to said interface means, and means for opening and closing said flowpath, in combination with a reversibly convertible assembly of flexible sheet material with means for converting said assembly between a case in a stage one case configuration for storing and transporting said breathing apparatus when not in use and a garment in a stage two garment configuration for supporting said source of breathing gas on the torso of the user when in use, comprising when in the stage one configuration:

a) a first element of flexible sheet material having at least two mating edges foldable to place said edges in close proximity to form said case;

b) a first fastening means for maintaining said edges in close proximity when said case is closed for transporting said apparatus, and for converting said assembly between stage one and stage two configurations;

c) second and third elements of flexible sheet material each of which lies interiorly of said case and is attached to said first element in the region of a respective one of said mating edges thereof; and d) means located interiorly of said first element at the base of said case when said case is closed for receiving said source of breathing gas and holding said source in place during transport; and further comprising in said stage two garment configuration, wherein said case is opened and unfolded the interior of said case comprising part of an exterior of said garment, and said second and third elements folded forwardly around the torso of the user, said first element lies at the rear of the user's torso forming armholes between said first element and said second and third elements respectively, and wherein said means for receiving said source of breathing gas is located on the back of the user, and said conduit means delivers breathing gas from said source to said interface means when said means for opening and closing said flowpath is in an open position; and e) a second fastening means for holding said second and third elements in place when folded around said user's torso.

4. The breathing assembly of claim 3, wherein said means for receiving and holding said gas source comprises a tubular pouch of flexible sheet material having an opening at one end.

5. The breathing assembly of claim 3, wherein said second fastening means comprises a respective plurality of strips of synthetic fiber fastening material attached to said second and third elements, said respective plurality of strips being overlaid in perpendicular directions when said second and third elements are folded about the torso of the user.

6. The breathing assembly of claim 3, comprising a separate openable compartment attached within said case for receiving said breathing interface means.

7. The breathing assembly of claim 6, wherein said separate compartment comprises a pouch of flexible sheet material attached to one of said second and third elements, said pouch in positioned at the front of the user's torso when said second and third elements are folded about the torso of the user.

8. The breathing assembly of claim 3 having means provided interiorly of said first element at the base of said case when said case is in the stage one configuration and exteriorly of said first element when said case is in the stage two configuration, for guiding said conduit means between said source of breathing gas and said interface means.

* * * * *